United States Patent

Singh et al.

Patent Number: 5,210,262
Date of Patent: May 11, 1993

[54] METHOD FOR PREPARING A PHOSPHONIC ACID ESTER

[75] Inventors: Janak Singh, Lawrenceville; Richard H. Mueller, Ringoes, both of N.J.

[73] Assignee: E. R. Squibb & Sons, Inc., Princeton, N.J.

[21] Appl. No.: 944,583

[22] Filed: Sep. 14, 1992

Related U.S. Application Data

[62] Division of Ser. No. 381,339, Jul. 17, 1989, Pat. No. 5,177,239.

[51] Int. Cl.$^5$ ............................. C07F 9/40; C07F 9/38
[52] U.S. Cl. ................................. 558/134; 558/136; 558/137; 558/161
[58] Field of Search ................. 558/134, 136, 137, 161

[56] References Cited

U.S. PATENT DOCUMENTS

3,733,379  5/1973  Szabo .................................. 558/189
4,014,959  3/1977  Crutchfield et al. ............... 558/180

OTHER PUBLICATIONS

Bronson, J. J. et al., "Synthesis and Antiviral Activity of the Nucleotide Analogue (S)-1-[3-Hydroxy-2-(-phosphonylmethoxy)-propyl]cystosine," *J. Med. Chem.* 1989, 32, 1457–1463.
Wilson, J. R. H. "Synthesis of Diethyl Alkoxymethlphosphonates via Lewis Acid Promoted Regiospecific Cleavage of Alkoxy-4-Chlorophenoxymethanes," *J. Chem. Soc.* Perkin Trans. I, 1986.
Chem. Abst. 92:186461Z (1980), p. 677, abstract of Petrov, K. A. et al., "Alkoxymethylation of dialkyl, ethylene, and diphenyl chlorophosphites with dialkyl formals".
Arbusov, A. I., *Akad. SSSR, Otd. chim.* 1959, 35, 38; engl. Ausg. S. 31, 33, 34 (Beilstein Handbuch, 4, Aufl., 4, Erg-Werk, Bd. I/5).
Kiyoshi et al., *Chemical Abstracts*, vol. 66, No. 38014 (1967).
Aldrich Catalog, p. 1087 (1990).
*The Chemist's Companion*, by A. J. Gordon and R. A. Ford, pp. 67–69 (1972).
Brown, *J. Am. Chem. Soc.*, 39, p. 3913 (1974).
Pudovik et al., *Chemical Abstracts*, vol. 69, No. 27492 (1968).
Zaripov et al., *Chemical Abstracts*, vol. 79, No. 78894 (1973).
Fieser and Fieser's *Reagents for Organic Synthesis*, vol. 10, p. 324 (1982).
Stork et al., *J. Am. Chem. Soc.*, 101, p. 7107 (1979).
Pudovik et al., *Zhurnal Obschei Khimii* (English Transl.) p. 678 (1968).
"Mechanism and Structure in Organic Chemistry" by Edwin S. Gould, pp. 286–291, (1959).
"Silicon in Organic Synthesis" by Ernest W. Colvin, pp. 321–323 (1981).

Primary Examiner—Mary C. Lee
Assistant Examiner—Michael G. Ambrose
Attorney, Agent, or Firm—Burton Rodney

[57] ABSTRACT

A method is provided for preparing a phosphonic acid ester having the structure

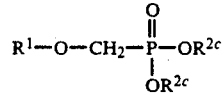

wherein $R^1$ is farnesyl or a derivative or analog thereof, and $R^2$ is lower alkyl, by treating a farnesyl halide $R^1Hal(Hal=Cl,Br,I)$ with an alkoxide of the structure

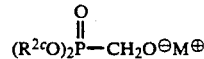

wherein M is an alkali metal and $R^{2c}$ is lower alkyl.

The resulting phosphonic acid ester is an intermediate in preparing a squalene synthetase inhibitor which is used for inhibiting cholesterol biosynthesis.

9 Claims, No Drawings

METHOD FOR PREPARING A PHOSPHONIC ACID ESTER

This is a division of application Ser. No. 381,339, filed Jul. 17, 1989, now U.S. Pat. No. 5,177,239.

FIELD OF THE INVENTION

A method is provided for preparing a phosphonic acid ester which is useful as an intermediate in the preparation of a squalene synthetase inhibitor.

BACKGROUND OF THE INVENTIONS

U.S. patent application Ser. No. 381,434 entitled "Phosphorus-Containing Squalene Synthetase Inhibitors and Method", filed concurrently herewith discloses phosphorus-containing squalene synthetase inhibitors which are useful in inhibiting cholesterol biosynthesis including those of the structure

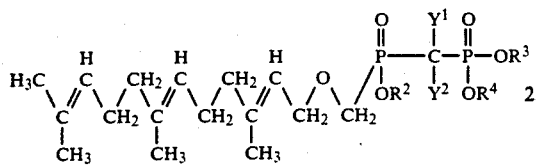

wherein $R^2$, $R^3$, and $R^4$ are H, metal ion, or lower alkyl and $Y^1$ and $Y^2$ are H or halogen. These compounds may be prepared starting with the phosphonic acid ester II

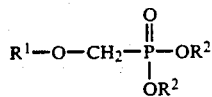   II wherein $R^2$ is $C_1$ to $C_8$ alkyl or $C_3$ to $C_{12}$ alkenyl.

BRIEF DESCRIPTION OF THE INVENTIONS

In accordance with the present invention, a method is provided for preparing phosphonic acid ester II, which method includes the steps of reacting a halide of the structure III $R^1$-Hal(Hal is Br, Cl or I)   III with an alkoxide (or metallated carbinol) of the structure

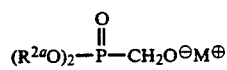   IV wherein $R^{2a}$ is $C_1$ to $C_8$ alkyl or $C_3$ to $C_{12}$ alkenyl (preferably alkyl ($R^{2c}$)), and M is an alkali metal such as cesium, potassium, sodium or lithium, preferably potassium, to form the phosphonic acid ester II and, if desired, recovering the phosphonic acid ester II from the reaction mixture.

The resulting phosphonic acid ester II may then be employed in preparing squalene synthetase inhibitors of structure I employing procedures as described in U.S. patent application Ser. No. 381,434, filed concurrently herewith.

In the above formulae II, III and IV, $R^1$ is $R^5$-$Q^1$-$Q^2Q^3$-wherein $Q^1$, $Q^2$ and $Q^3$ are independently:

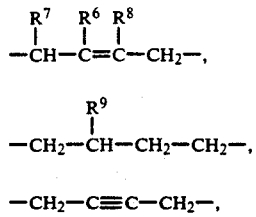

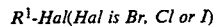

or a bond, with the stipulation that if $Q^1$ is a bond, then $Q^2$ and $Q^3$ must be bonds, and if $Q^2$ is a bond, then $Q^3$ is a bond; $R^6$ is H, lower alkyl, halo or haloalkyl (e.g. $CH_2F$, $CF_3$); $R^7$ is H, halogen, lower alkyl or alkylthio; $R^8$ is H, halogen, trimethylsilyl or lower alkyl; $R^9$ is H, or lower alkyl;

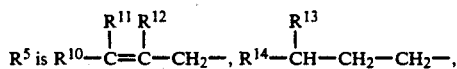

$R^{16}$—C≡C—$CH_2$— (wherein $R^{16}$ is lower alkyl or H), or $CH_3(CH_2)_p$— where p is 2 to 7; $R^{10}$ and $R^{11}$ are independently hydrogen, lower alkyl such as methyl or ethyl, halogen, lower alkenyl or haloalkyl or $R^{10}$ and $R^{11}$ can be taken together to form $(CH_2)_s$, where s is 2 to 7; $R^{12}$ is hydrogen, lower alkyl, halogen or lower alkenyl; $R^{13}$ and $R^{14}$ are independently lower alkyl such as methyl or ethyl; with the proviso that if all of $Q^1$, $Q^2$ and $Q^3$ are bonds, then both $R^{10}$ and $R^{11}$ cannot be H, and $R^5$ cannot be $CH_3(CH_2)_p$—, with $p \leq 4$.

The compounds prepared in accordance with the method of the invention include all stereoisomers thereof.

Unless otherwise indicated, the term "lower alkyl" or "alkyl" as employed herein alone or as part of another group includes both straight and branched chain hydrocarbons containing 1 to 8 carbons in the normal chain, preferably 1 to 4 carbons, such as methyl, ethyl, propyl, isopropyl, butyl, t-butyl, isobutyl, pentyl, hexyl or isohexyl.

The term "lower alkenyl" or "alkenyl" as used herein by itself or as part of another group refers to straight or branched chain radicals of 2 to 12 carbons, preferably 3 to 6 carbons in the normal chain, which include one double bond in the normal chain, and which may include an aryl or alkyl substituent, such as vinyl, 2-propenyl, 2-butenyl, 3-phenyl-2-propenyl, 2-pentenyl, 2-hexenyl, 2-heptenyl, 2-octenyl, 2-nonenyl, 2-decenyl, 2-undecenyl, 2-dodecenyl and the like.

The term "halogen" or "halo" as used herein refers to chlorine, bromine, fluorine, and iodine with chlorine or fluorine being preferred.

The term "haloalkyl" as used herein refers to any of the lower alkyl groups defined above substituted with a halogen as defined above, for example $CH_2F$, $CF_3$ and the like.

The term "metal ion" refers to alkali metal ions such as sodium, potassium, cesium or lithium and alkaline earth metal ions such as magnesium and calcium.

DETAILED DESCRIPTION OF THE INVENTION

In carrying out the method of the invention, a solution of carbinol V

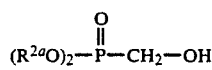

V wherein is $C_1$-$C_8$ alkyl or $C_3$ to $C_{12}$ alkenyl, in an inert organic solvent such as tetrahydrofuran, monoglyme, diethyl ether, benzene, toluene and the like, preferably tetrahydrofuran, is treated with a solution of strong base such as of the structure A or A'.

$$MN[Si(Alkyl)_3]_2 \quad A$$

$$MN(Alkyl)_2 \quad A'$$

wherein M is an alkali metal such as potassium, sodium or lithium, preferably potassium, or LiH, NaH or KH, in an inert organic solvents such as tetrahydrofuran, monoglyme, diethyl ether, benzene, toluene and the like, preferably tetrahydrofuran, under an inert atmosphere such as argon, at a temperature within the range of from about $-78°$ C. to about $50°$ C., preferably from about $-20°$ C. to about $20°$ C., to form the alkoxide IV.

A solution of halide III in a dry inert organic solvent such as tetrahydrofuran, monoglyme, diethyl ether, benzene, toluene and the like, preferably tetrahydrofuran, is treated with the alkoxide IV at a temperature within the range of from about $-78°$ C. to about $50°$ C., and preferably from about $-20°$ C. to about $20°$ C., to form the phosphonic acid ester II.

A 1:1 molar ratio of halide III and alkoxide IV will usually be employed, although, if desired, an excess of either reactant may be used.

In a preferred embodiment of the method of the present invention, a solution of carbinol VA

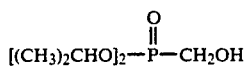

VA in an inert organic solvent, which preferably is tetrahydrofuran, is treated with a strong base, preferably, potassium bis(trimethylsilyl)amide in an inert organic solvent, which preferably is tetrahydrofuran, under an inert atmosphere, such as argon or nitrogen, to form alkoxide IVA

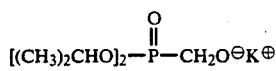

IVA

A solution of farnesyl chloride in an inert organic solvent, which preferably is tetrahydrofuran, is reacted with the alkoxide IVA at a temperature within the range of from about $-10$ to about $10°$ C., employing a 1:1 molar ratio of alkoxide:farnesyl chloride to form the phosphonic acid derivative of the structure IIA

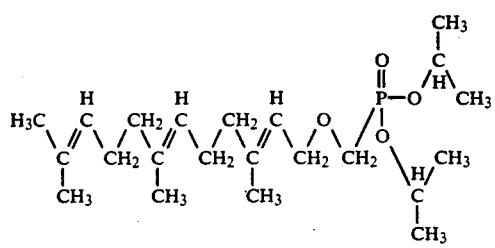

IIA

The carbinol V may be prepared by treating phosphite VI $$(R^{2a}O)_2POH \quad VI$$

with paraformaldehyde and an organic base such as triethylamine, tributylamine or ethyl diisopropylamine at a temperature within the range of from about $70°$ to about $120°$ C., under an inert atmosphere, such as argon or nitrogen, to form carbinol V.

Examples of starting material III, that is $R^1$-Hal, suitable for use herein include the following which either are known in the literature or are simple derivatives of known compounds prepared by employing conventional procedures.

It will be appreciated that the compounds listed in the following table represent all possible stereoisomers.

$$R^1\text{-Hal}(Hal=Cl, Br \text{ or } I)$$

wherein $R^1$ is $R^5$-$Q^1$-$Q^2$-$Q^3$- as follows in A. through F.

A. 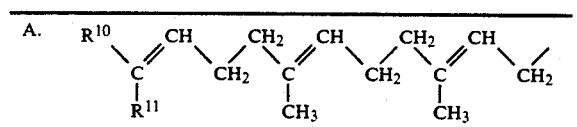

| | $R^{10}$ | $R^{11}$ |
|---|---|---|
| 1. | $C_2H_5$ | $CH_3$ |
| 2. | $CH_3$ | $C_2H_5$ |
| 3. | $n$-$C_3H_7$ | $CH_3$ |
| 4. | $CH_3$ | $n$-$C_4H_9$ |
| 5. | $t$-$C_4H_9$ | $CH_3$ |
| 6. | —$(CH_2)_{s'}$— $s' = 4$ to $6$ | |
| 7. | H | H |
| 8. | F | F |
| 9. | Cl | Cl |
| 10. | $CH_2F$ | $CH_3$ |
| 11. | —$CH=CH_2$ | H |

B. 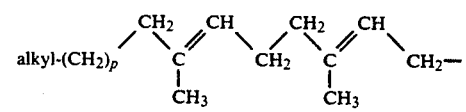

1. $\dfrac{\text{alkyl}(CH_2)_p-}{CH_3(CH_2)_p-}$ where p is 3 to 7

2. 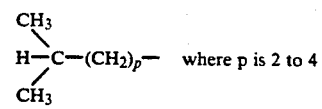 where p is 2 to 4

C.
1. 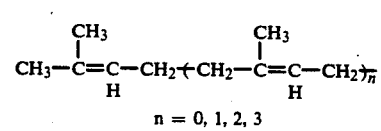

n = 0, 1, 2, 3

2. 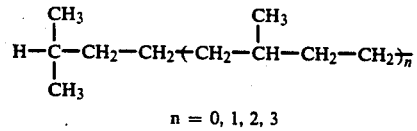

n = 0, 1, 2, 3

D. $R^1$ is

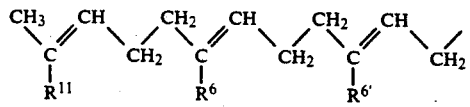

-continued

|   | R¹¹ | R⁶ | R⁶' |
|---|---|---|---|
| 1. | C₂H₅ | C₂H₅ | CH₃ |
| 2. | CH₃ | CH₃ | C₂H₅ |
| 3. | CH₃ | C₂H₅ | C₂H₅ |
| 4. | C₂H₅ | C₂H₅ | C₂H₅ |
| 5. | CH₃ | C₂H₅ | CH₃ |
| 6. | CH₃ | H | CH₃ |
| 7. | CH₃ | CH₃ | H |
| 8. | H | H | H |

E. R¹ is

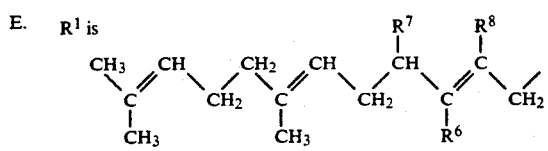

|   | R⁷ | R⁶ | R⁸ |
|---|---|---|---|
| 1. | H | I | H |
| 2. | H | H | I |
| 3. | H | CH₃ | CH₃ |
| 4. | CH₃S | CH₃ | H |
| 5. | F | CH₃ | H |
| 6. | CH₃ | CH₃ | H |
| 7. | H | CH₃ | CH₃ |
| 8. | H | CH₃ | Cl |
| 9. | H | CF₃ | H |
| 10. | H | Cl | H |
| 11. | H | CH₃ | (CH₃)₃Si |
| 12. | H | CH₃ | F |

F. Other examples of R¹ include the following

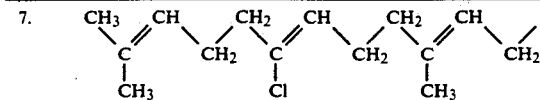

7. 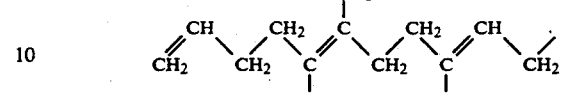

8. 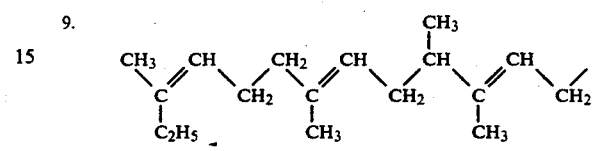

9. 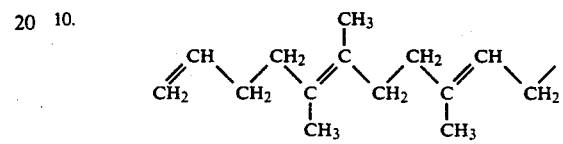

10. 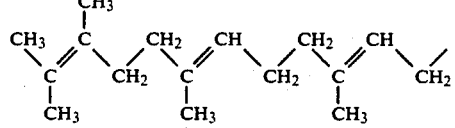

11. 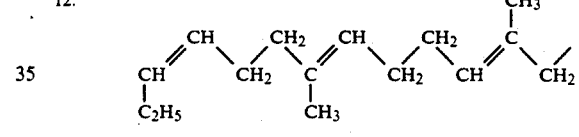

12. 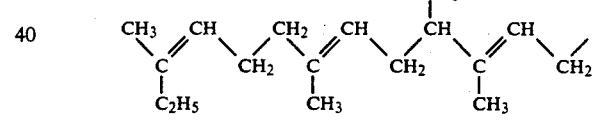

13. 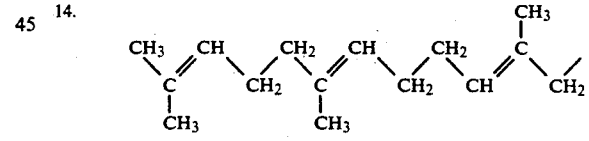

14.

15. 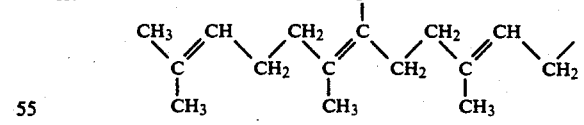

16. 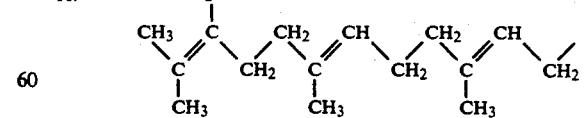

The phosphonic ester of formula II may be employed to prepare squalene synthetase inhibitors in accordance with the following reaction sequences.

Scheme I

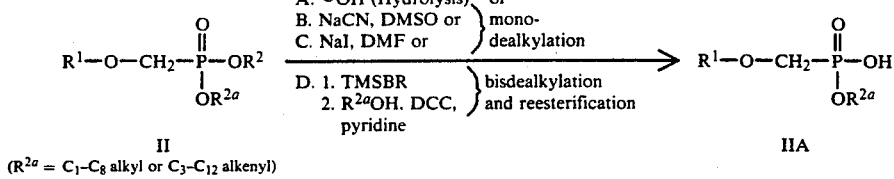

II
($R^{2a}$ = $C_1$–$C_8$ alkyl or $C_3$–$C_{12}$ alkenyl)

Scheme II

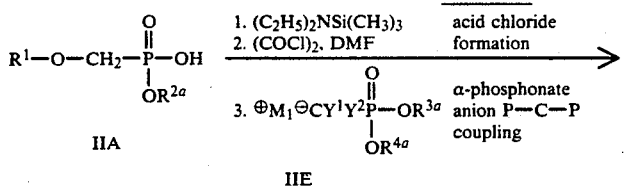

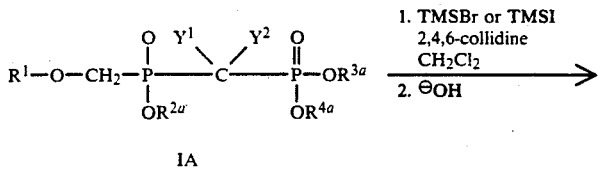

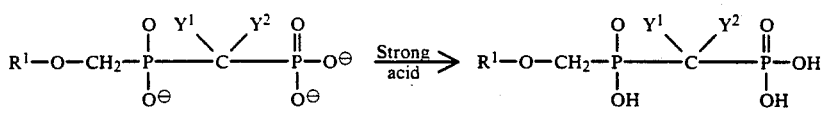

Scheme III

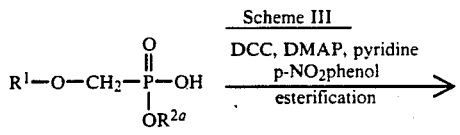

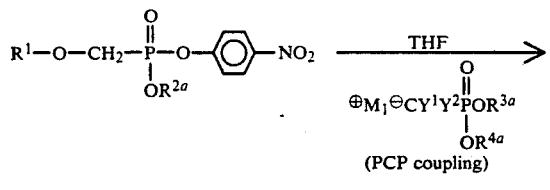

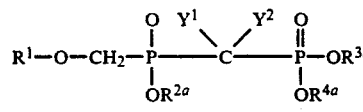

As seen in Reaction Schemes I, II and III, compounds of formula IA where $Y^1$ and $Y^2$ are H or halogen, $R^{2a}$, $R^{3a}$ and $R^{4a}$ are independently H, metal ion, $C_1$ to $C_8$ alkyl or $C_3$ to $C_{12}$ alkenyl, may be prepare in accordance with the following method of the invention starting with diester II.

The diester II may be converted to the corresponding monoester IIA by any of four methods (A, B, C or D) as discussed below.

In Method A, diester II is treated with a strong aqueous base such as NaOH, KOH, CsOH, or LiOH, typically in the presence of a solvent such as dioxane, isopropanol, methanol or ethanol at a temperature within the range of from about 25° to about 125° C. to form monoester IIA.

In Methods B and C, diester II is subjected to a monodealkylation by treatment with sodium cyanide, potassium cyanide, cesium cyanide, or lithium cyanide and a solvent such as dimethyl sulfoxide or dimethylformamide (Method B) or with sodium iodide, lithium iodide, cesium iodide, or lithium chloride in the presence of a solvent such as dimethylformamide, dimethyl sulfoxide or acetone, the above reactions being carried out at a temperature of within the range of from about 40° to about 160° C., to form monoester IIA.

In Method D, diester II is subjected to a bisdealkylation by treating II with bromotrimethylsilane under an inert atmosphere such as argon or nitrogen in the presence of 2,4,6-collidine or triethylamine in dichloromethane and then reesterifying by reacting with an alcohol in the presence of dicyclohexylcarbodiimide (DCC) and an organic base such as pyridine, or 4-dimethylaminopyridine (DAP) to form monoester IIA.

As seen in Reaction Scheme II, compounds of formula I may be prepared in accordance with the following method of the invention starting with monoester IIA which is dissolved in an inert organic solvent such as dichloromethane and treated, under an inert atmosphere such as argon, with N,N-diethyltrimethylsilylamine. After evaporation of solvent, the residue is dissolved in dichloromethane or an aromatic solvent such as benzene or toluene, or other appropriate inert organic solvent, preferably containing dimethylformamide as a catalyst, under an inert atmosphere such as argon, and oxalyl chloride is added thereto. The reaction mixture is evaporated to give acid chloride IIC

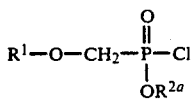

IIC

An α-phosphonate anion P-C-P coupling is carried out on the acid chloride IIC as follows.

To a stirred solution of an optionally substituted dialkyl methyl phosphonate

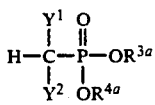

IID wherein $Y^1$, and $Y^2$ are as defined hereinbefore and $R^{3a}$ and $R^{4a}$ are independently $C_1$–$C_8$ alkyl or $C_3$–$C_{12}$ alkenyl, in an inert organic solvent such as tetrahydrofuran, cooled to a temperature within the range of from about $-90°$ C. to about $0°$ C., is added a strong base, such as n-butyl lithium or lithium diisopropylamide, in hexane, tetrahydrofuran or other inert organic solvent under an inert atmosphere such as argon, followed in some instances by transmetallation by the addition of a metal halide, such as $CeCl_3$, $ZnCl_2$, $MgBr_2$, CuI, to form the metal salt IIE

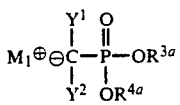

IIE wherein $M_1$ is $Li^+$, $Na^+$, $K^+$, $^+MgHal$, $^+ZnHal$, $^+Ce(Hal)_2$ or $^+Cu$ wherein Hal is a halogen ion such as $Cl^-$, $Br^-$ or $I^-$.

The metal salt IIE is maintained at a reduced temperature as described above and acid chloride IIC in an inert organic solvent such as tetrahydrofuran or diethyl ether is added to form the phosphinyl-phosphonate IA. The metal salt IIE will be employed in a molar ratio to acid chloride IIC of within the range of from about 1.0:1 to about 2.5:1 and preferably from about 1.8:1 to about 2.4:1. Triester IA, in an inert organic solvent such as methylene chloride, may then be subjected to dealkylation by treating with excess bromotrimethylsilane or iodotrimethylsilane in the presence of 2,4,6-collidine or bis(trimethylsilyl)trifluoroacetamide or bistrimethylsilylacetamide and then treating with an inorganic base such as aqueous NaOH, LiOH or Mg(OH)$_2$, optionally in the presence of an alcohol such as methyl alcohol, to form the salt IB which may be separated out by chromatography. Salt IB may be treated with a strong acid such as HCl to form acid IC.

As seen in Reaction Scheme III, compounds of formula I may be prepared according to the following method of the invention starting with monoester IIA which is dissolved in pyridine, and treated with p-nitrophenol and 4-dimethylaminopyridine and dicyclohexyl carbodiimide, under an inert atmosphere such as argon, at 25°60° C. (employing a molar ratio of phenol: IIA of within the range of from about 0.8:1 to about 1.2:1) to form the p-nitrophenyl ester IIB.

An α-phosphonate anion P-C-P coupling is carried out on nitrophenyl ester IIB by reacting nitrophenyl ester IIB with metal salt IIE in a manner similar to that described above for IA to form the phosphinyl-phosphonate IA The metal salt IIE will be employed in a molar ratio to p-nitrophenyl ester IIB of within the range of from about 1.0:1 to about 2.5:1 and preferably from about 1.8:1 to about 2.4:1.

The triester IA may be hydrolyzed to the corresponding monoester ID as follows.

Triester IA may be treated with strong inorganic base such as KOH, NaOH or LiOH in H$_2$O or H$_2$O/alcohol mixtures, or with nucleophiles such as, NaCN, KCN, NaI, LiCl, or LiBr in dimethylformamide or dimethylsulfoxide, under an inert atmosphere such as argon, employing a molar ratio of base or nucleophile to triester of within the range of from about 2:1 to about 10:1, and at a temperature within the range of from about 25° to about 160° C. to form the monoester ID

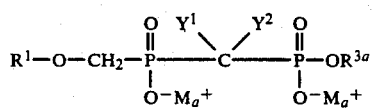

ID where $M_a$ is an alkali metal.

The phosphonic acid ester II is useful in the synthesis of squalene synthetase inhibitors of structure I, prepared as described in U.S. patent application Ser. No. 381,434 filed concurrently herewith, and as described below.

The squalene synthetase inhibitors of formula I may be employed to inhibit cholesterol biosynthesis by inhibition of the de novo squalene production. These compounds inhibit the squalene synthetase enzyme and, in addition, some of the compounds of formula I inhibit other enzymes in the pathway from isopentenyl diphosphate to squalene, that is, farnesyl diphosphate synthetase and isopentenyl diphosphate—dimethylallyl diphosphate isomerase.

Thus, the compounds of formula I are useful in treating atherosclerosis to inhibit progression of disease and in treating hyperlipidemia to inhibit development of atherosclerosis. In addition, the compounds of formula I may increase plasma high density lipoprotein cholesterol levels.

As squalene synthetase inhibitors, the formula I compounds may also be useful in inhibiting formation of gallstones and in treating tumors.

The following Examples represent preferred embodiments of the present invention Unless indicated otherwise, all temperatures are expressed in °C.

EXAMPLE 1

(E,E)-[[(3,7,11-Trimethyl-2,6,10-dodecatrienyl)-oxy]-methyl]phosphonic acid, bis(1-methylethyl) ester A. (Hydroxymethyl)phosponic acid, bis(1-methylethyl) ester A mixture of 33.2 g (0.20 mol) of diisopropyl phosphite, 2.8 ml (0.02 mol) of triethylamine, and 6.0 g (0.20 mol) of paraformaldehyde, was immersed in a 100° C. oil bath and then heated between 100°–120° C. for 45 minutes under nitrogen. An exotherm occurred within 10 minutes and all of the paraformaldehyde dissolved rapidly. The triethylamine was removed at reduced pressure, and the residue was bulb-to-bulb distilled in four portions to provide a total of 35.17 g (91) of title compound as a colorless oil.

TLC silica gel (5:95 CH$_3$OH:CH$_2$Cl$_2$) Rf=0.17

$^1$H NMR (CDCl$_3$, 270 MHz)

δ 4.73 (sextet, 3H, J=6 Hz)

3.84 (d, 2H, J=6 Hz)

1.34 (d, 12H, J=6 Hz)ppm.

$^{13}$C NMR (CDCl$_3$, 67.8 MHz)

57.5 (d, J=162 Hz)

23.8 (d, J=6 Hz) ppm

B. (E,E)-Farnesyl chloride

A solution of N-chlorosuccinimide (6.8 g, 50.9 mmol) in dry dichloromethane (338 ml) was cooled to −30° and dimethylsulfide (4.1 ml, 55.3 mmol) was added dropwise over 3 min. After 13 min., the cooling bath was removed and the mixture was stirred for 30 min. The mixture was cooled to −40° and a solution of (E,E)-farnesol (11.3 ml, 44 mmol) in 112 ml dichloromethane was added over 10 min. The cooling bath was removed and the mixture was stirred for 30 min. The temperature of the reaction mixture rose to 0° and a clear solution was obtained. After stirring for two more hours the solvent (about 400 ml) was removed on a rotary evaporator and the material was taken up in hexane (600 ml). The solution was washed with ice cold water (3×90 ml) and cold brine (2×35 ml) and then dried (MgSO$_4$). The solvent was removed under vacuum at ambient temperature and finally dried under pump vacuum to give 11.0 g (100%) of title compound as a pale yellow liquid.

C.
(E,E)-[[(3,7,11-Trimethyl-2,6,10-dodecatrienyl)oxy]methyl]phosphonic acid, bis(1-methylethyl) ester A solution of potassium bis(trimethylsilyl)amide (1.4M in tetrahydrofuran (THF), 14.3 ml, 20 mmol) was added dropwise over 5 min. to a solution of [(CH$_3$)$_2$CHO]$_2$P(O)CH$_2$OH (3.92 g, 20 mmol) in THF (40 ml) at ice bath temperature under argon. A precipitate formed in 3 minutes After 10 min a solution of Part B (E,E)-farnesyl chloride (4.82 g, 20 mmol) in dry THF (10 ml) was added dropwise over 4 min. and the mixture was stirred for 2.5 hours at 0° C. and for 3 hours at room temperature. The reaction was quenched with acetic acid (1.2 g., 20 mmol). The mixture was poured into ethyl acetate (EtOAc) (50 ml) and washed twice with 30 ml 50% brine and 30 ml brine. The organic layer was dried (MgSO$_4$) and solvent was evaporated to give 8.1 g (100%) of crude title product. The product was purified by flash column chromatography over silica gel (200 g). The column was prepared in hexane; the material was charged neat and eluted successively with 0.1 liter hexane, 4 liter 25% EtOAc/hexane and 1 liter 50% EtOAc/hexane). Fractions 53 to 108 (45 ml each) were combined and evaporated to give 5.6 g (yield 70%) of title product. Forerun fractions 44 to 52 (45 ml each) were combined and evaporated to give 0.4 g (yield 5%) of slightly impure title product.

Anal. Cal'd for C (MW 400.54)

C, 65.97; H, 10.32; P, 7.73; H$_2$O, 0.0

Found C, 66.03; H, 10.32; P, 7.67; H$_2$O, 0.01 (KF)

$^{13}$C NMR (67.8 MHz, CDCl$_3$): 141.5, 135.3, 131.1, 124.3, 123.7, 119.9, 70.8 (d, J=6 Hz), 69.1 (d, J=12 Hz), 64.0 (d, J=168 Hz), 39.6, 39.5, 26.7, 26.2, 25.6, 24.0 (d, J=4 Hz), 23.9 (d, J=4 Hz), 17.6, 16.4, 15.9 ppm.

TLC, silica gel: a. EtOAc/hexane, 1:1, (UV and PMA, heat), R$_f$s:farnesyl chloride 0.8, carbinol 0.03, title product 0.24. b. Acetone/hexane, 4:1, R$_f$s:farnesyl chloride 0.87, carbinol 0.41, title product 0.73.

EXAMPLE 2

(E,E)-[[(3,7,11-Trimethyl-2,6,10-dodecatrienyl)oxy]methyl]phosphonic acid, diethyl ester

A. (Hydroxymethyl)phosphonic acid, diethyl ester

The procedure of Kluge was followed (Org. Syn. 1986, Vol. 64, 80–84). The following ingredients were combined: 69 g (0.50 mol) of diethyl phosphite, 15 g (0.50 mol) of paraformaldehyde, and 5.1 g (0.05 mol) of triethylamine. The stirred mixture was immersed in a preheated oil bath at 120° C. and heated for one hour. Upon cooling, the triethylamine was removed on the rotary evaporator at 80° C., and the residue was then distilled bulb-to-bulb (150°–160° C., 0.10 mm) to provide 57.5 g (68) of title compound as a colorless liquid.

TLC: Silica gel (5:95 CH$_3$OH:CH$_2$Cl$_2$) R$_f$=0.19

1HH NMR (CDCl$_3$) (270 MHz)

δ 4.95 (br, 1H)

4.09 (quint, 4H, J=7 Hz)

3.83 (d, 2H, J=5.8 Hz)

1.27 (t, 6H, J=7 Hz) ppm.

$^{13}$C NMR (CDCl$_3$) (67.8 MHz)

δ 6 62.2 (d, J=7.6 Hz)

56.5 (d, J=162.8 Hz)

16.1 (d, J=5.7 Hz) ppm.

B.
(E,E)-[[(3,7,11-Trimethyl-2,6,10-dodecatrienyl)oxy]methyl]phosphonic acid, diethyl ester Following the procedure of Example 1 part C except substituting the Example 2, Part A carbinol for the carbinol employed in Example 1 Part C, the title compound is obtained.

EXAMPLE 3

(E,E)-[[(1-Methylethoxy)[[(3,7,11-trimethyl-2,6,10-dodecatrienyl)oxy]methyl]phosphinyl]methyl]phosphonic acid, dimethyl ester

A.
(E,E)-[[(3,7,11-Trimethyl-2,6,10-dodecatrienyl)oxy]methyl]phosphonic acid, mono(1-methylethyl) ester To a solution of 1.57 g (3.91 mmol) of Example 1 ester in 20 ml of 2-propanol under argon was added 20 ml of 1 N KOH, and the reaction was heated to 105° C. for 48 hours. After cooling to room temperature, the 2-propanol was evaporated and the aqueous residue was stirred with dichloromethane and acidified with 10% HCl. The organic layer was washed with water and brine, dried (MgSO$_4$), and evaporated to provide 1.39 g (96%, corrected for 0.37 mole equiv. of dichloromethane) of title compound as a colorless oil.

TLC Silica gel (8:1:1 1-propanol:con NH$_3$:H$_2$O) R$_f$=0.55.

$^1$H NMR (CDCl$_3$, 270 MHz)

δ 5.28 (t, 1H, J=7 Hz)

5.09 (m, 2H)

4.72 (m, 2H)

4.12 (d, 2H, J=7 Hz)

3.70 (d, 2H, J=7 Hz)

2.06 (m, 8H)

1.67 (s, 6H)

1.60 (s, 6H)

1.33 (d, 6H, J=6 Hz) ppm.

B.
(E,E)-[[(1-Methylethoxy)][(3,7,11-trimethyl-2,6,10-dodecatrienyl)oxy]-methyl]phosphinyl]methyl]phosphonic acid, dimethyl ester To a stirred solution of 1.395 g (3.89 mmol) of Part A compound in 8 ml of dichloromethane under argon was added 1.5 ml (7.51 mmol) of distilled N,N-diethyl(trimethylsilyl)amine. The reaction was allowed to stir for 1.5 hours at room temperature, the solvent was evaporated and the residue was dissolved in benzene, evaporated and then pumped at high vacuum. The remainder was dissolved in 8 ml of dichloromethane containing three drops of dimethylformamide (DMF) under argon at 0° C., and 0.68 ml (7.8 mmol) of distilled oxalyl chloride was added dropwise over 10 minutes, with much gas evolution. After 45 minutes at 0° C., the reaction was allowed to warm to room temperature for 45 minutes. The solution was evaporated and the residue was twice dissolved in benzene and evaporated, followed by pumping at high vacuum.

To a solution of 0.93 ml (8.58 mmol) of dimethyl methylphosphonate in 22 ml of THF at −78° C. under argon was added 5.2 ml (8.36 mmol) of n-butyllithium in hexane over 5 minutes to give a white suspension. After 40 minutes, the acid chloride prepared above was added in 8 ml of THF over 10 minutes. The reaction was allowed to stir for one hour at −78° C., when it was quenched with saturated ammonium chloride and diluted with diethyl ether. The aqueous layer was made acidic with 10% HCl and the organic layer was separated and washed with brine. The aqueous layer was re-extracted with dichloromethane, and the dichloromethane layer was washed with brine. The combined organic layers were dried (MgSO$_4$) and evaporated to provide 1.84 g of a crude yellow oil. Flash chromatography on 200 g of silica gel eluted with 2.98 methanol:dichloromethane gave 1.49 g (82%) of pure title triester as a cooless oil.

TLC Silica gel (5:95 CH$_3$OH:CH$_2$Cl$_2$) R$_f$=0.21

IR (CCl$_4$) 2977, 2954, 2926, 2853, 1449, 1385, 1375, 1256, 1229, 1063, 1036, 992, 841 cm$^{-1}$.

$^1$H NMR (CDCl$_3$, 270 MHz)

δ 5.32 (t, 2H, J=7 Hz)

5.09 (m, 2H)

4.78 (m, 2H)

4.10 (d, 2H, J=7 Hz)

3.79, 3.83 (two d, 6H, J=6 Hz)

3.6–3.9 (m, 2H)

2.50 (m, 2H)

2.07 (m, 8H)

1.68 (s, 6H)

1.60 (s, 6H)

1.34, 1.37 (two d, 6H, J=7 Hz) ppm.

Mass Spec (CI-CH$_4$, +ions) m/e 505 (M+C$_3$H$_5$), 493 (M+C$_2$H$_5$), 465 (M+H).

EXAMPLE 4

(E,E)-[[Hydroxy[[(3,7,11-trimethyl-2,6,10-dodecatrienyl)oxy]methyl]phosphinyl]methyl]phosphonic acid, tripotassium salt To a stirred solution of 654 mg (1.42 mmol) of Example 3 triester in 7 ml of dry dichloromethane at room temperature was added 0.47 ml (3.54 mmol) of 2,4,6-collidine followed by 0.94 ml (7.09 mmol) of bromotrimethylsilane. The reaction was allowed to stir for 23 hours at room temperature, the solution was evaporated, the residue was dissolved in benzene, evaporated, and pumped at high vacuum. The remainder was dissolved in 8 ml of 1M KOH, stirred for 30 minutes, diluted with water and lyophilized. The crude material was purified by MPLC on a column of CHP20P (2.5 cm diameter×20 cm height) eluted with water (fractions 1–12), followed by a gradient created by the gradual addition of acetonitrile (500 ml) to a reservoir of 400 ml of water. Approximately 15 ml fractions were collected. Fractions 27–33 were combined, the acetonitrile was evaporated at reduced pressure, and the aqueous solution was lyophilized to provide 680 mg (93%) of title product in the form of a dense, amorphous white lyophile. Further drying under vacuum led to an insignificant loss of mass. The pH of a 1% w/v solution was 8.9.

TLC Silica gel (5:4:1 1-propanol:conc. NH$_3$:H$_2$O) R$_f$=0.44.

IR (KBr) 3400 (broad), 2967, 2921, 2860, 1662, 1445, 1381, 1180, 1146, 1085, 1054, 967, 867, 789, 466 cm$^{-1}$.

$^1$H NMR (D$_2$O, 270 MHz)

δ 5.34 (t, 1H, J=7 Hz)

5.07, 5.08 (two t, 2H, J=7 Hz)

4.07 (d, 2H, J=7 Hz)

3 57 (d, 2H, J=6.4 Hz)

1.8–2.2 (m, 10H)

1.64 (s, 3H)

1.60 (s, 3H)

1.54 (s, 6H) ppm.

$^{13}$C NMR (67.8 MHz, D$_2$O): 144.35, 37.63, 134.48, 125.46, 125.30, 120.50, 70.17 (d, J=11.36 Hz), 69.30 (d, J=113.55 Hz), 39.9, 39.8, 30.45 (dd, J=119.23 Hz, 79.48 Hz) 26.78, 26.64, 25.89, 17.99, 16.74, 16.29 ppm.

$^{31}$P NMR (D$_2$O, 36.2 MHz)

δ 32.1 (d, J=9.6 Hz)

12.7 (d, J=9.6 Hz) ppm.

Mass Spec (FAB, +ions) m/e 509 (M+H).

Analysis Calcd for C$_{17}$H$_{29}$K$_3$P$_2$O$_6$+0.37 mol H$_2$O (Effective MW=515.3): C, 39.61; H, 5.83; P, 12.02

Found: C, 39.98; H, 5.99; P, 12.29

What is claimed is:

1. A method for preparing a compound having the structure $$R^1-O-CH_2-\overset{\overset{O}{\|}}{\underset{\underset{OR^{2a}}{|}}{P}}-\overset{\overset{Y^1}{|}}{\underset{\underset{Y^2}{|}}{C}}-\overset{\overset{O}{\|}}{\underset{\underset{OR^{4a}}{|}}{P}}-OR^{3a}$$

wherein

Y$^1$ and Y$^2$ are H or halogen;

R$^{2a}$, R$^{3a}$ and R$^{4a}$ may be the same or different and are independently C$_1$ to C$_8$ alkyl or C$_3$ to C$_{12}$ alkenyl;

R$^1$ is R$^5$-Q$^1$-Q$^2$-Q$^3$- wherein Q$^1$, Q$^2$ and Q$^3$ are the same or different and are independently $$-\overset{\overset{R^7}{|}}{C}H-\overset{\overset{R^6}{|}}{C}=\overset{\overset{R^8}{|}}{C}-CH_2-, \quad -CH_2-\overset{\overset{R^9}{|}}{C}H-CH_2-CH_2-,$$

$$-CH_2-C\equiv C-CH_2-$$

or a single bond, with the proviso that if Q$^1$ is a bond, then Q$^2$ and Q$^3$ are bonds, and if Q$^2$ is a bond then Q$^3$ is a bond, and wherein R$^6$ is H, lower alkyl, halo or haloalkyl; R$^7$ is H, halogen, lower alkyl or lower alkylthio; R$^8$ is H, halogen, trimethylsilyl or lower alkyl; and R$^9$ is H or lower alkyl;

$R^5$ is 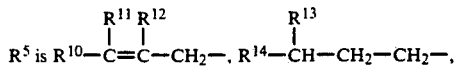

$CH_3(CH_2)_p$ where p is an integer from 2 to 7 or $R^{16}-C\equiv C-CH_2-$ where $R^{16}$ is H or lower alkyl; $R^{10}$, and $R^{11}$ are the same or different and are independently H, lower alkyl, haloalkyl, halogen or lower alkenyl or $R^{10}$ and $R^{11}$ can be taken together to form $(CH_2)_s$ where s is an integer from 2 to 7; $R^{12}$ is H, lower alkyl, halogen or lower alkenyl; and $R^{13}$ and $R^{14}$ are the same or different and are independently lower alkyl; with the proviso that if all of $Q^1$, $Q^2$ and $Q^3$ are bonds, then both $R^{10}$ and $R^{11}$ cannot be H, and $R^5$ cannot be $CH_3(CH_2)_p$- with p less than or equal to 4, and including all stereoisomers thereof, which comprises treating a solution of a carbinol of the structure

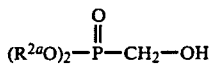

in an inert organic solvent, with a strong base which has the structure

at a temperature of within the range of from about $-20°$ C. to about 20° C., under an inert atmosphere, to form an alkoxide of the structure

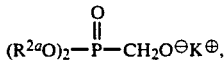

reacting an allylic halide of the structure

wherein Hal is Cl, Br or I, wherein $R^1$ is as defined above, with said alkoxide, at a temperature within the range of from about $-20°$ C. to about 20° C., to form the phosphonic acid diester of the structure

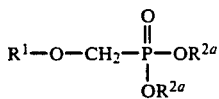

treating the phosphonic acid diester with a strong aqueous base, an alkali metal cyanide or an alkali metal halide or treating said diester with bromotrimethylsilane or iodotrimethylsilane, under an inert atmosphere, in the presence of 2,4,6-collidine, and then treating with an alcohol of the formula

and dicyclohexylcarbodiimide to form the monoester

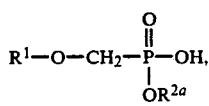

treating the monoester with diethyl(trimethylsilyl)amine, under an inert atmosphere, treating and resulting reaction product with oxalyl chloride to form the acid chloride, and treating the acid chloride with a metal salt of the structure

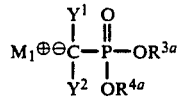

where $M_1$ is $Li^+$, $Na^+$, $K^+$, MgHal, +ZnHal, $Ce(Hal)_2$ or $Cu^+$, and $R^{3a}$ and $R^{4a}$ are independently selected from $C_1-C_8$ alkyl or $C_3-C_{12}$ alkenyl, to form the phosphinyl-phosphonate of the formula

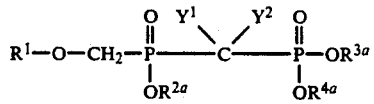

2. The method of claim 1 which further comprises for preparing a compound of the structure

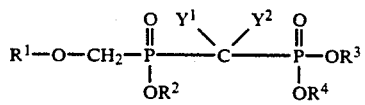

wherein $R^2$, $R^3$ and $R^4$ represent a metal ion or H, which comprises treating a phosphinyl-phosphonate of the formula

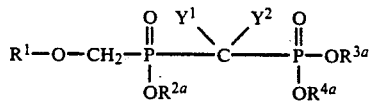

wherein $R^{2a}$, $R^{3a}$ and $R^{4a}$ are independently $C_1-C_8$alkyl or $C_3-C_{12}$alkynyl, with a dealkylating agent, and then treating with an inorganic base to form the salt of the formula

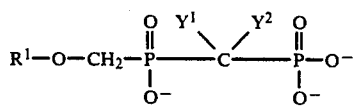

and, optionally, treating the salt with a strong acid to form the corresponding acid.

3. A method for preparing a compound having the structure

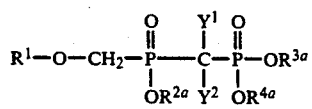

wherein
$Y^1$ and $Y^2$ are H or halogen;
$R^{2a}$, $R^{3a}$ and $R^{4a}$ may be the same or different and are independently $C_1$ to $C_8$ alkyl or $C_3$ to $C_{12}$ alkenyl;
$R^1$ is $R^5-Q^1-Q^2-Q^3-$ wherein $Q^1$, $Q^2$ and $Q^3$ are the same or different and are independently

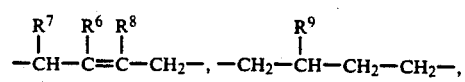

-continued $-CH_2-C\equiv C-CH_2-$ or a single bond, with the proviso that if $Q^1$ is a bond, then $Q^2$ and $Q^3$ are bonds, and if $Q^2$ is a bond then $Q^3$ is a bond, and wherein $R^6$ is H, lower alkyl, halo or haloalkyl; $R^7$ is H, halogen, lower alkyl or lower alkylthio; $R^8$ is H, halogen, trimethylsilyl or lower alkyl; and $R^9$ is H or lower alkyl;

$R^5$ is $R^{10}-\overset{R^{11}}{\underset{|}{C}}=\overset{R^{12}}{\underset{|}{C}}-CH_2-$, $R^{14}-\overset{R^{13}}{\underset{|}{C}}H-CH_2-CH_2-$, $CH_3(CH_2)_p$ where p is an integer from 2 to 7, or $R^{16}-C\equiv C-CH_2-$ where $R^{16}$ is H or lower alkyl, $R^{10}$, and $R^{11}$ are the same or different and are independently H, lower alkyl, haloalkyl, halogen or lower alkenyl or $R^{10}$ and $R^{11}$ can be taken together to form $(CH_2)_s$ where s is an integer from 2 to 7; $R^{12}$ is H, lower alkyl, halogen or lower alkenyl; and $R^{13}$ and $R^{14}$ are the same or different and are independently lower alkyl with the proviso that if all of $Q^1$, $Q^2$ and $Q^3$ are bonds, then both $R^{10}$ and $R^{11}$ can be $CH_3(CH_2)_p-$ with p less than or equal to 4, and including all stereoisomers thereof, which comprises treating a solution of a carbinol of the structure $$(R^{2a}O)_2-\overset{O}{\underset{\|}{P}}-CH_2-OH$$

in an inert organic solvent, with a strong base which has the structure $KN[Si(Alkyl)_3]_2$ at a temperature of within the range of from about $-20°$ C. to about $20°$ C., under an inert atmosphere, to form an alkoxide of the structure $$(R^{2a}O)_2-\overset{O}{\underset{\|}{P}}-CH_2O^{\ominus}K^{\oplus},$$

reacting an allylic halide of the structure $R^1Hal$ wherein Hal is Cl, Br or I, wherein $R^1$ is as defined above, with said alkoxide, at a temperature within the range of from about $-20°$ C. to about $20°$ C., to form the phosphonic acid diester of the structure $$R^1-O-CH_2-\overset{O}{\underset{\underset{OR^{2a}}{|}}{\overset{\|}{P}}}-OR^{2a}$$

treating the phosphonic acid diester with a strong aqueous base, an alkali metal cyanide or an alkali metal halide or treating said diester with bromotrimethylsilane or iodotrimethylsilane, under an inert atmosphere, in the presence of 2,4,6-collidine, and then treating with an alcohol of the formula $R^{2a}OH$ and dicyclohexylcarbodiimide to form the monoester $$R^1-O-CH_2-\overset{O}{\underset{\underset{OR^{2a}}{|}}{\overset{\|}{P}}}-OH$$

treating said monoester in pyridine, with p-nitrophenol and 4-dimethylaminopyridine and dicyclohexylcarbodiimide, under an inert atmosphere, to form the nitrophenol of the formula

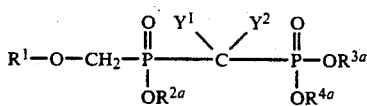

and treating the nitrophenol with a metal salt of the structure $$M_1^{\oplus\ominus}\overset{Y^1}{\underset{\underset{Y^2}{|}}{C}}-\overset{O}{\underset{\underset{OR^{4a}}{|}}{\overset{\|}{P}}}-OR^{3a}$$

where $M_1$ is Li+, Na+, K+, MgHal, +ZnHal, Ce(Hal)$_2$ or Cu+, and $R^{3a}$ and $R^{4a}$ are independently selected from $C_1-C_8$ alkyl or $C_3-C_{12}$ alkenyl, to form the phosphinyl-phosphonate of the formula

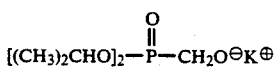

4. The method as defined in claim 3 wherein the reaction of the allylic halide which is farnesyl chloride and alkoxide which has the formula $$[(CH_3)_2CHO]_2-\overset{O}{\underset{\|}{P}}-CH_2O^{\ominus}K^{\oplus}$$

is carried out at a temperature within the range of form about $-10°$ C. to about $10°$ C.

5. The method as defined in claim 1 where the reaction of the allylic halide which is farnesyl chloride and the alkoxide which has the formula $$[(CH_3)_2CHO]_2-\overset{O}{\underset{\|}{P}}-CH_2O^{\ominus}K^{\oplus}$$

is carried out at a temperature within the range of from about $-10°$ C. to about $10°$ C.

6. The method as defined in claim 1 wherein the strong base is $KN[Si(CH_3)_3]_2$.

7. The method as defined in claim 3 wherein the strong base has the structure $KN[Si(CH_3)_3]_2$.

8. The method as defined in claim 1 wherein the diester has the structure

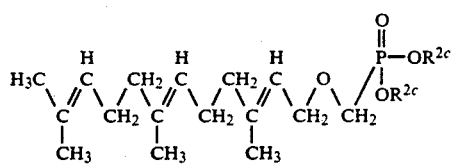
wherein R²ᶜ is lower alkyl.
9. The method as defined in claim 3 wherein the phosphonic acid diester is
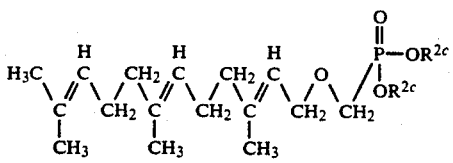
wherein R²ᶜ is lower alkyl.

UNITED STATES PATENT AND TRADEMARK OFFICE
CERTIFICATE OF CORRECTION

PATENT NO. : 5,210,262
DATED : May 11, 1993
INVENTOR(S) : Janak Singh et al

It is certified that error appears in the above-identified patent and that said Letters Patent is hereby corrected as shown below:

Column 16, line 9, change "MgHal" to --$\overset{+}{\text{M}}$gHal-- and "Ce(Hal)$_2$" to --$\overset{+}{\text{C}}$e(Hal)$_2$--

Column 17, line 25, delete "can" and replace with --cannot be H and R$^5$ cannot--

Column 18, line 29, change "MgHal" to --$\overset{+}{\text{M}}$gHal-- and "Ce(Hal)$_2$" to --$\overset{+}{\text{C}}$e(Hal)$_2$--

Signed and Sealed this

First Day of March, 1994

Attest:

BRUCE LEHMAN

Attesting Officer

Commissioner of Patents and Trademarks